United States Patent
Weaver et al.

(10) Patent No.: US 7,221,977 B1
(45) Date of Patent: May 22, 2007

(54) METHOD AND APPARATUS FOR MEASURING BATTERY DEPLETION IN IMPLANTABLE MEDICAL DEVICES

(75) Inventors: Lyle Weaver, Woodside, CA (US); Charles Neder, Mountain View, CA (US); Louis Wong, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 389 days.

(21) Appl. No.: 10/877,215

(22) Filed: Jun. 25, 2004

(51) Int. Cl.
*A61N 1/00* (2006.01)

(52) U.S. Cl. .............................. 607/29; 607/34; 607/4; 320/136

(58) Field of Classification Search .................. 607/29, 607/34; 320/166, 167
See application file for complete search history.

(56) References Cited

U.S. PATENT DOCUMENTS

| | | | |
|---|---|---|---|
| 3,895,284 A * | 7/1975 | Schweizer et al. | 320/134 |
| 5,405,363 A * | 4/1995 | Kroll et al. | 607/5 |
| 5,458,624 A | 10/1995 | Renirie et al. | 607/29 |
| 5,534,015 A * | 7/1996 | Kroll et al. | 607/7 |
| 6,167,309 A | 12/2000 | Lyden | 607/29 |
| 6,169,673 B1 * | 1/2001 | McIntyre et al. | 363/59 |
| 2001/0034541 A1 | 10/2001 | Lyden | 607/29 |
| 2002/0140404 A1 | 10/2002 | Lyden | 320/166 |

FOREIGN PATENT DOCUMENTS

| | | |
|---|---|---|
| EP | 0 647 455 B1 | 7/2001 |
| WO | WO 99/14612 | 3/1999 |

* cited by examiner

*Primary Examiner*—Carl Layno
*Assistant Examiner*—Brian T. Gedeon
(74) *Attorney, Agent, or Firm*—Steven M. Mitchell (57) ABSTRACT

A method and apparatus for measuring battery depletion in an implantable medical device is presented. The apparatus includes first and second switch pairs disposed in series between the battery and a load, and connected in a parallel arrangement with respect to one another. A capacitor is connected in a first polarity between the battery and the load when only first and fourth switches are closed and in a second polarity when only second and third switches are closed. A comparator circuit causes the switches to reverse the capacitor's polarity based on a comparison of the voltage drop across the capacitor to a threshold value. A counter counts the number of times the capacitor reverses polarity, which is proportional to the amount of charge transferred from the battery during its lifetime in the device and indicative of the battery's level of depletion.

20 Claims, 7 Drawing Sheets

METHOD AND APPARATUS FOR MEASURING BATTERY DEPLETION IN IMPLANTABLE MEDICAL DEVICES

BACKGROUND OF THE INVENTION

1. Field of the Invention

The present invention relates generally to battery-powered devices and, more particularly, to measuring battery depletion in battery-powered implantable medical devices.

2. Background Art

Implantable medical devices, such as implantable cardiac devices (ICDs) (e.g., pacemakers, cardioverters, and defibrillators), implantable neurostimulator devices, blood glucose monitoring/delivery devices, etc., are typically battery powered. The state of battery depletion can be monitored or estimated in order to determine the elective replacement (ER) and end-of-life (EOL) points, which enable a physician to schedule appropriate device replacement.

One approach for determining battery depletion is to monitor the battery terminal voltage during the lifetime of the battery in the implantable medical device. Typically the battery terminal voltage decreases as the battery is depleted until a threshold voltage is reached, indicating that the battery needs to be replaced. A problem with this approach is some battery chemistries, such as carbon monofloride, have terminal characteristics, including terminal voltage and source impedance, which do not change according to the battery's state of depletion. Additionally, monitoring changes in the battery's terminal voltage might not be an accurate indicator of the battery's state of depletion because the change in terminal voltage between a new battery and a battery at EOL is relatively small, typically 0.2 V.

Another approach for determining battery depletion is to measure the total integrated current (Ampere-hours) drawn from the battery during its lifetime in the implantable medical device. Measuring the total integrated current to determine battery depletion is useful for battery chemistries, such as carbon monofloride, which have terminal characteristics that do not change according to the battery's state of depletion. Additionally, by recording the total integrated current on a daily, weekly, or other periodic basis, a measure of the rate of battery depletion (which may increase or decrease over time depending upon the programmed patient therapy and physiological needs) may also be determined. The measure of the rate of battery depletion is clinically useful in predicting when the battery will reach the ER or EOL points.

A conventional current integrating circuit for measuring total integrated current drawn from a battery in an implantable medical device is a voltage-controlled oscillator driven by a resistor coupled between the battery and a battery reservoir capacitor. A problem with this approach is it operates over a limited dynamic range of current drawn from the battery. For example, a current integrating circuit in an ICD should be capable of integrating lower background current drawn by ICD sensing electronics that is typically less than 10 μA, as well as higher current bursts drawn for burst pacing or high speed telemetry that are typically greater than 1 mA.

A disadvantage of conventional voltage-controlled oscillator current integrating circuits is that they require multiple passive elements (i.e., resistors) in order to accommodate a wide dynamic range of current drawn from the battery. Furthermore, because the voltage drop across passive elements in conventional voltage-controlled oscillator current integrating circuits is dependent on the average current through them, the conventional circuits suffer from reduced accuracy when integrating over a wide dynamic range of current drawn from the battery.

What is needed are a better method and apparatus for determining the state of depletion of a battery in an implantable medical device for a wide dynamic range of current drawn from the battery.

BRIEF SUMMARY OF THE INVENTION

The present invention is directed to a method and apparatus for measuring the total integrated current drawn from a battery in order to determine the battery's state of depletion over a wide dynamic range of current drawn from the battery. The present invention is particularly useful in the environment of a battery-powered implantable medical device. Example embodiments of the present invention are described below.

In an embodiment of the present invention, a method for measuring the total integrated current drawn over time from a battery in an implantable medical device includes the steps of: (1) monitoring a voltage across a capacitor serially connected between the battery and a load; (2) comparing the voltage to a threshold value; (3) switching the capacitor's polarity when the voltage exceeds the threshold value; and (4) counting the number of times the capacitor switches polarity. The number of times the capacitor switches polarity is proportional to the amount of charge transferred from the battery during its lifetime in the implantable medical device.

In another embodiment of the present invention, an apparatus for measuring the total integrated current drawn over time from a battery in an implantable medical device includes first and second switch pairs disposed in parallel between the battery and a load. Each switch pair includes two switches connected in series. The first switch pair has first and second switches connected to one another at a first node, and the second switch pair has third and fourth switches connected to one another at a second node. The apparatus further includes a capacitor connected between the first and second nodes such that the capacitor is connected in a first polarity between the battery and the load when only the first and fourth switches are closed and in a second polarity when only the second and third switches are closed. In this manner, the switches and capacitor are connected in an "H-bridge" configuration.

The apparatus further includes a comparator circuit, which causes the switches to reverse the capacitor's polarity based on a comparison of the voltage across the capacitor to a threshold value. The apparatus further includes a counter that counts the number of times the capacitor reverses polarity, which is indicative of the total integrated current drawn from the battery.

The method and apparatus can operate over a wide dynamic range of current drawn from a battery in an implantable medical device because the voltage drop across the switched capacitor element is independent of the average current through it. The method and apparatus can also more accurately determine the battery's state of depletion because the switched capacitor element allows for a bigger voltage drop across it without incurring the power dissipation lost to a resistor. Additionally, the method and apparatus can be implemented with a single passive element, resulting in less power dissipation than would be experienced if multiple passive elements were used to measure the total integrated current drawn from the battery.

Further features and advantages of the present invention as well as the structure and operation of various example embodiments of the present invention are described in detail below with reference to the accompanying drawings.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention. In the drawings, like reference numbers indicate identical or functionally similar elements.

DETAILED DESCRIPTION OF THE INVENTION

Overview

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

Before describing the present invention in detail, it is helpful to describe an example environment in which the present invention may be implemented. The present invention is particularly useful in the environment of a battery-powered implantable medical device, such as an implantable cardiac device (ICD), implantable neurostimulator device, blood glucose monitoring/delivery device, and other battery-powered devices.

Figure 1:
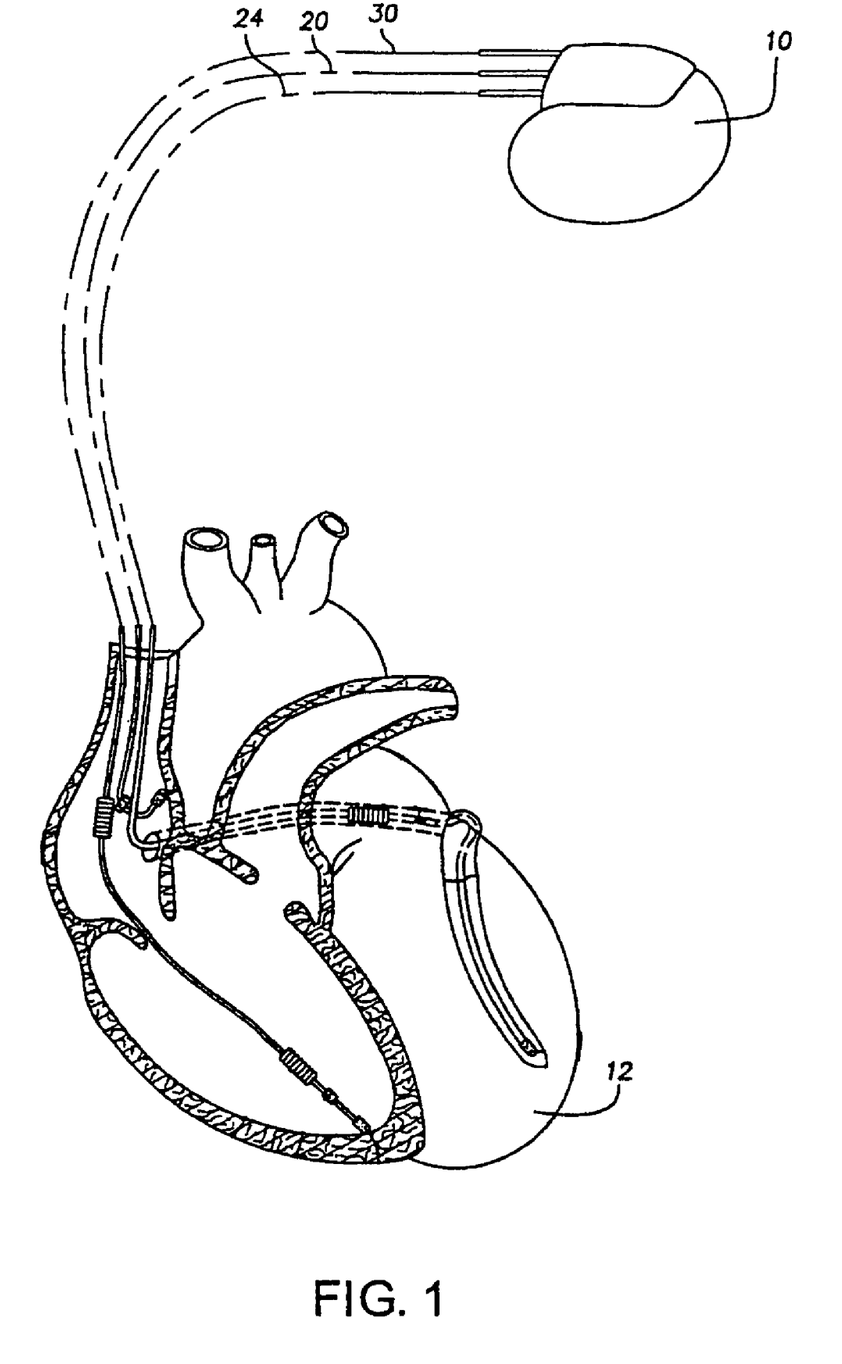
FIG. 1 is a simplified diagram of an exemplary battery-powered implantable medical device, and illustrates an ICD in electrical communication with at least three leads implanted into a patient's heart for delivering multi-chamber stimulation and shock therapy.
Figure 2:
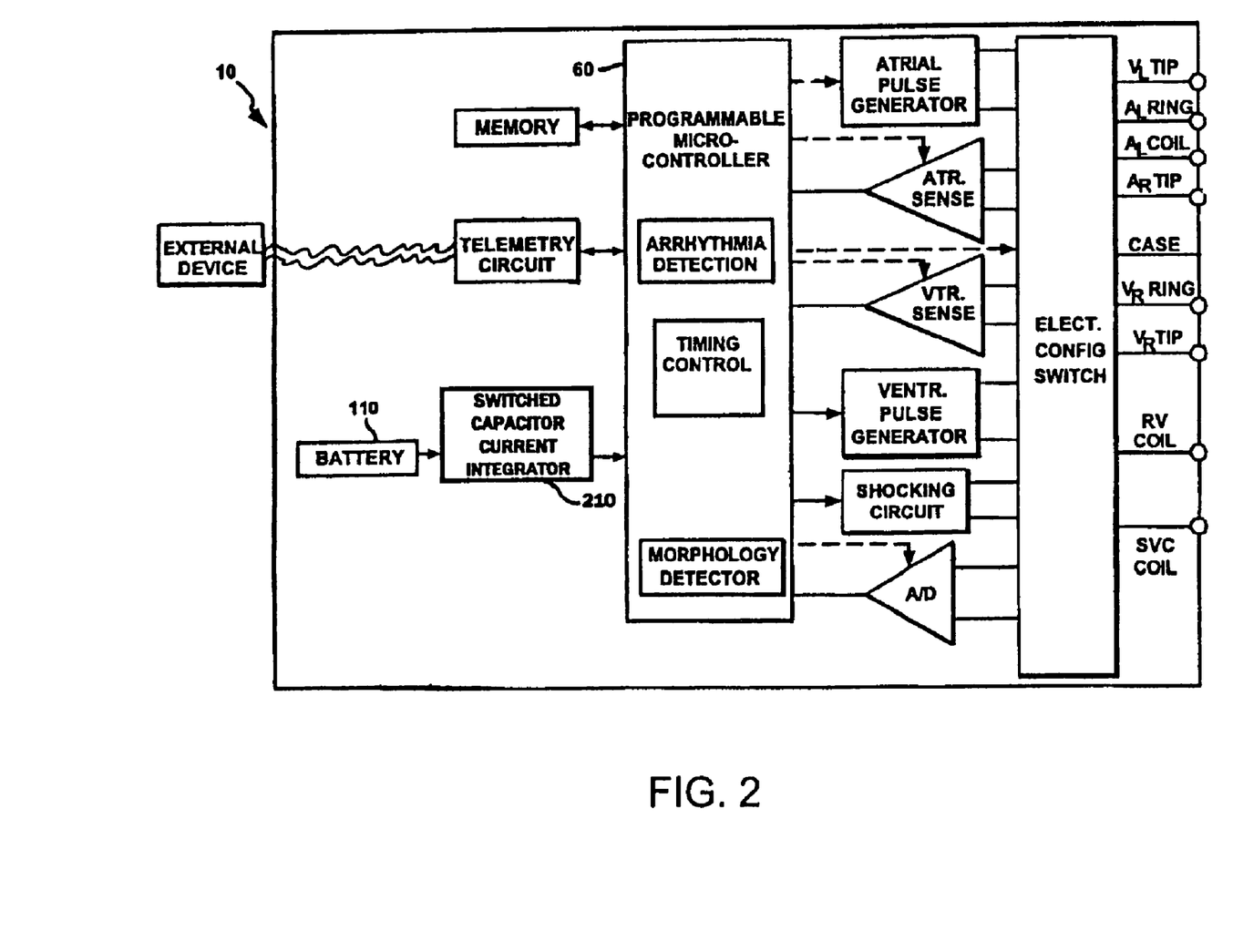
FIG. 2 is a functional block diagram of the ICD of FIG. 1 that incorporates a switched capacitor current integrator circuit, according to an example embodiment of the present invention

For example, an ICD is a medical device that is implanted in a patient to monitor electrical activity of a heart and to deliver appropriate electrical therapy (e.g., pacing pulses, cardioverting, and defibrillator pulses) and drug therapy, as required. ICDs include, for example, pacemakers, cardioverters, defibrillators, implantable cardioverter defibrillators, and the like. The term "implantable cardiac device" or simply "ICD" is used herein to refer to any implantable cardiac device. FIGS. 1 and 2 illustrate an exemplary ICD, in which the present invention can be implemented.

Exemplary ICD in Electrical Communication with a Patient's Heart

As shown in FIG. 1, an exemplary ICD 10 is in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20. To sense left atrial and ventricular cardiac signals and to provide left chamber pacing therapy, ICD 10 is coupled to coronary sinus lead 24. ICD 10 is also shown in electrical communication with the patient's heart 12 by way of an implantable right ventricular lead 30 capable of receiving cardiac signals and delivering stimulation in the form of pacing and shock therapy to the right ventricle.

Functional Elements of an Exemplary ICD

FIG. 2 shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

At the core of ICD 10 is a programmable microcontroller 60, which controls the various modes of stimulation therapy. As is well known in the art, microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory.

The details of the design of microcontroller 60 are not critical to the present invention. Rather, any suitable microcontroller 60 can be used to carry out the functions described herein. The use of microprocessor-based control circuits for performing timing and data analysis functions are well known in the art. In an example embodiment of the present invention, microcontroller 60 performs some of the steps associated with measuring the depletion of a battery 110 of ICD 10.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the ICD's and their inter-relationship, see U.S. Pat. No. 4,788,980 (Mann et. al.). The '052, '555, '298 and '980 patents are incorporated herein by reference.

As shown in FIG. 2, microcontroller 60 controls an atrial pulse generator, a ventricular pulse generator, and atrial and ventricular sensing circuits, to trigger or inhibit delivery of pacing stimulation pulses, as is well known in the art. When ICD 10 operates as a cardioverter, pacer or defibrillator, microcontroller 60 further controls a shocking circuit capable of generating shocking pulses of low (up to about 0.5 Joules), moderate (about 0.5–10 Joules), or high energy (about 11 to 40 Joules). Microcontroller 60 can also control an analog-to-digital (A/D) data acquisition system, configured to acquire intracardiac electrogram signals and convert the raw analog data into a digital signal.

As shown in FIG. 2, microcontroller 60 can include arrhythmia detection and morphology detection circuitry to recognize and classify arrhythmia in order to deliver appropriate therapy to a patient. Microcontroller 60 can further include timing control circuitry to control pacing parameters (e.g., the timing of stimulation pulses) and monitor the timing of refractory periods, PVARP intervals, noise detection windows, evoked response windows, alert intervals, marker channel timing, etc., which are well known in the art.

In the example of FIG. 2, ICD 10 further includes a plurality of switches for connecting desired electrodes to appropriate I/O circuits in response to a control signal from microcontroller 60, as is known in the art. ICD 10 further includes a memory, which stores and modifies, as required, the programmable operating parameters used by microcontroller 60 to customize the operation of ICD 10 to suit the needs of a particular patient. Also shown in FIG. 2 as part of ICD 10 is a telemetry circuit for communicating intracardiac electrograms and status information relating to the operation of ICD 10 to an external device through an established communication link.

Also shown in FIG. 2 as part of ICD 10 is battery 110, which provides operating power to a load that includes all of the circuits shown in FIG. 2. Because ICD 10 employs shocking therapy, battery 110 must be capable of operating at low current drains for long periods of time, and then be capable of providing high-current pulses (for capacitor charging) when the patient requires a shock pulse. Because the lower current drains occur over much longer periods of time than the higher current drains, the lower current drains typically account for a significant portion of battery 110 consumption. Elective replacement time of battery 110 may be determined by monitoring the level of battery 110 depletion. In an embodiment, battery 110 is a lithium/silver vanadium oxide battery but other battery chemistries can also be used.

In an example embodiment of the present invention, ICD 10 further includes a switched capacitor current integrator 210, which measures the total integrated current drawn from battery 110 in order to determine the level of battery 110 depletion. Switched capacitor current integrator 210 is further shown in FIGS. 3A–3C and 4A–4B and described in detail below. FIG. 5 further illustrates a method for measuring the total integrated current drawn from battery 110 in order to determine the level of battery 110 depletion.

ICD 10 consumes current over a wide dynamic range according to the mode of operation. In an embodiment, ICD 10 can draw current from battery 110 over the range of about 10 µA to 10 mA. For example, ICD 10 can draw much more than 1 mA for burst pacing or high speed telemetry and 10 µA or less for powering ICD 10 sensing electronics. Battery current consumption is normally in the µA range for pacemakers with peaks occurring during the generation of the pacing pulses. Other battery functions can draw 10 mA or more from battery 110 and, for a cardioverter or defibrillator, the capacitor charging current is typically about 3 A.

In an embodiment, ICD 10 further includes a bypass circuit (not shown in FIG. 2), which bypasses switched capacitor current integrator 210 when high current peaks (e.g., tens of milliamperes to several amperes) are drawn from battery 110, such as during shocking treatment (e.g., defibrillation), reformation of the shocking capacitors, and exercise of battery 110. When switched capacitor current integrator 210 is bypassed, microcontroller 60 can adjust the measure of battery 110 depletion accordingly. Switched capacitor current integrator 210 accurately determines the level of battery 110 depletion by accumulating the total integrated current over a wide dynamic range of current consumed by ICD 10.

Apparatus for Measuring Total Integrated Current and Battery Depletion

Figure 3A:
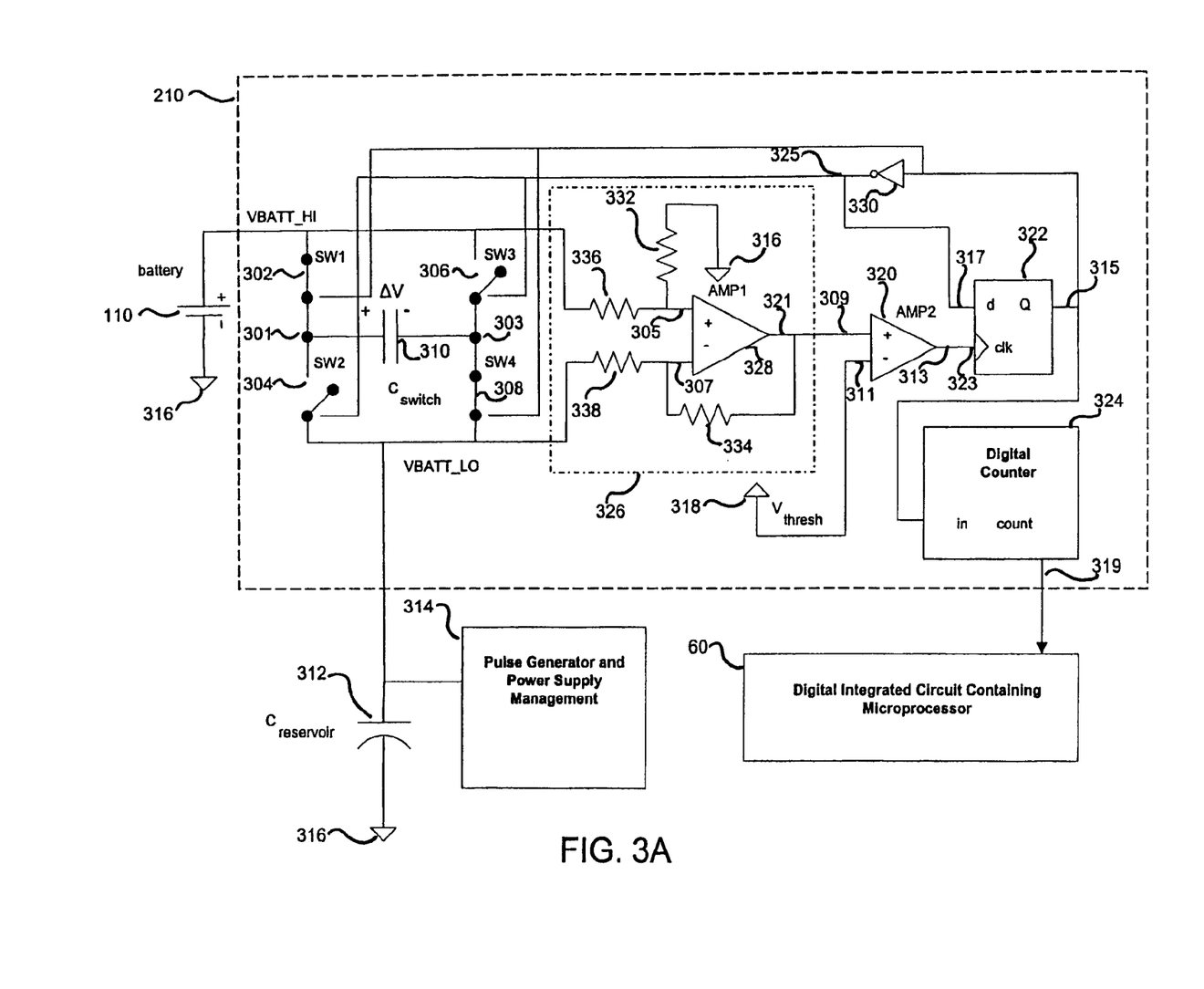
FIG. 3A is a high-level circuit diagram of a switched capacitor current integrator circuit, according to an example embodiment of the present invention.

FIG. 3A is a block diagram of switched capacitor current integrator circuit 210, in accordance with an example embodiment of the present invention. While switched capacitor integrator 210 is described with respect to the example environment of ICD 10, shown in FIG. 2, switched capacitor current integrator 210 can also be implemented in other battery-powered devices. Switched capacitor current integrator 210 includes a switched capacitor 310 and an array of four switches having a first switch 302, a second switch 304, a third switch 306, and a fourth switch 308. Switched capacitor current integrator 210 also includes a differential amplifier circuit 326, a comparator 320, and a flip-flop 322. A digital counter 324 is optionally included in switched capacitor current integrator 210 or in programmable microcontroller 60, shown in detail in FIG. 2.

Switched capacitor current integrator 210 is coupled between battery 110 and a load 314, which includes, for example, all of the circuits shown in FIG. 2. In an embodiment, battery 110 voltage VBATT_HI is approximately 2.8 V Load 314 draws current from battery 110, causing battery 110 to deplete over time. A reservoir capacitor 312 is shown in FIG. 3A coupled between load 314 and a ground 316. Reservoir capacitor 312 acts as a low-pass filter. Reservoir capacitor 312 can either be a discrete component, as shown in FIG. 3A, or may simply be represented by capacitance inherently present in load 314. In an embodiment, reservoir capacitor 312 has a capacitance of approximately 47 µF.

First through fourth switches 302–308 are arranged in an H-bridge configuration with switched capacitor 310. First and second switches 302 and 304 are coupled to each other at a first node 301 so that they are disposed in series between battery 110 and load 314. Third and fourth switches 306 and 308 are coupled to each other at a second node 303 so that they are disposed in series between battery 110 and load 314. First and second switches 302 and 304 are arranged in parallel with third and fourth switches 306 and 308. Switched capacitor 310 is coupled between first node 301 and second node 303 and alternates between first and second polarities according to whether first through fourth switches 302–308 are open or closed. A differential voltage drop ΔV across switched capacitor 310 is approximately equal to VBATT_HI minus VBATT_LO.

Figure 3B:
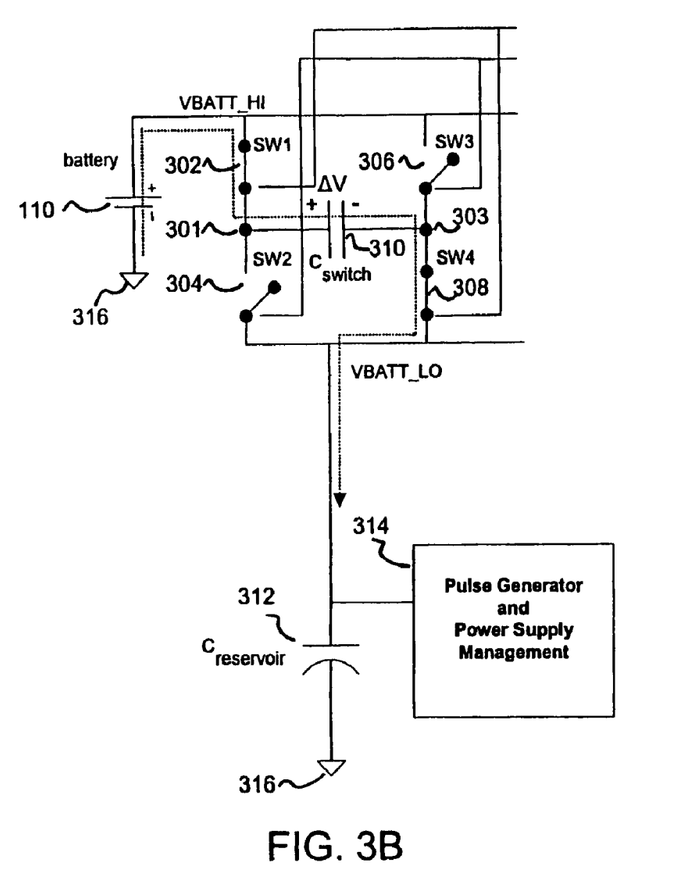
FIGS. 3B–3C illustrate two different configurations for an array of switches shown in the high-level switched capacitor current integrator circuit of FIG. 3A, according to example embodiments of the present invention.
Figure 3C:
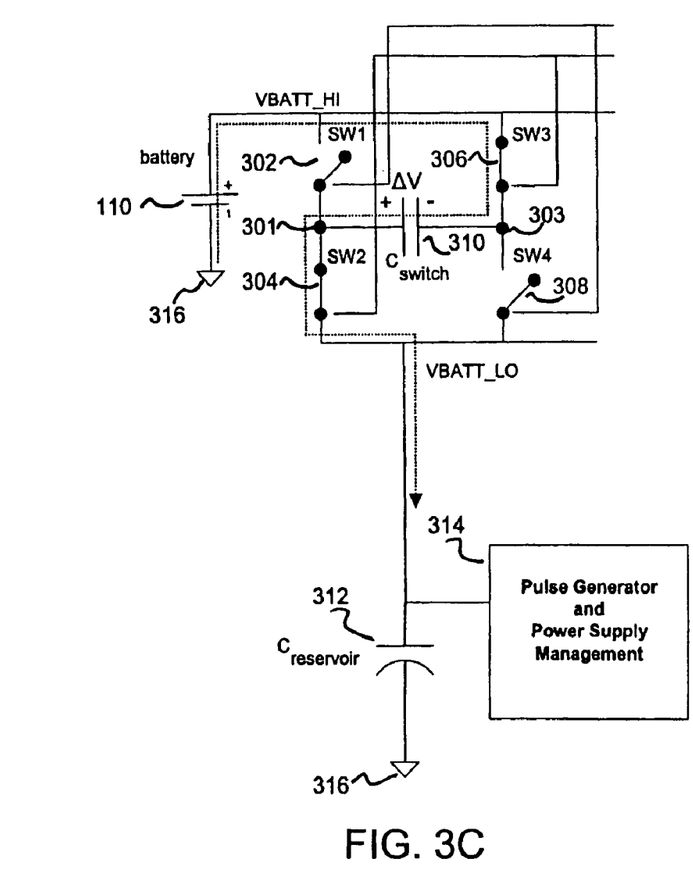

For example, as shown in FIG. 3B, switched capacitor 310 is connected between battery 110 and load 314 in the first polarity when first and fourth switches 302 and 308 are closed, and second and third switches 304 and 306 are open. In FIG. 3B, VBATT_LO is approximately VBATT_HI minus the differential voltage drop ΔV across switched capacitor 310. In an embodiment, the differential voltage drop ΔV across switched capacitor 310 is approximately 50 mV. Accordingly, if VBATT_HI is 2.8 V then VBATT_LO is approximately 2.75 V As shown in FIG. 3C, switched capacitor 310 is connected between battery 110 and load 314 in the second polarity when first and fourth switches 302 and 308 are open, and second and third switches 304 and 306 are closed. In FIG. 3C, VBATT_LO is approximately VBATT_HI plus the differential voltage drop ΔV across switched capacitor 310. In an embodiment, the differential voltage drop ΔV across switched capacitor 310 is approximately 50 mV. Accordingly, if VBATT_HI is 2.8 V then VBATT_LO is approximately 2.85 V just before charge redistributes between switched capacitor 310 and reservoir capacitor 312.

As shown in FIG. 3A, differential amplifier circuit 326 includes an amplifier 328. Amplifier 328 has a non-inverting input 305 coupled through a resistor 336 to battery 110, and an inverting input 307 coupled through a resistor 338 to load 314. A resistor 332 is coupled between non-inverting input 305 and ground 316, and a feedback resistor 334 is coupled between inverting input 307 and an amplifier output 321. Differential amplifier circuit 326 amplifies the differential voltage drop ΔV across switched capacitor 310.

Comparator 320 has a non-inverting input 309 coupled to amplifier output 321. Comparator 320 also has an inverting input 311 coupled to a threshold voltage supply $V_{thresh}$ 318. Comparator 320 compares the amplified differential voltage drop ΔV across switched capacitor 310 to $V_{thresh}$ 318. A comparator output 313 goes high when the differential voltage drop ΔV across switched capacitor 310 exceeds $V_{thresh}$ 318. For example, when load 314 of ICD 10 consumes electrical power, reservoir capacitor 312 becomes depleted and the differential voltage drop ΔV across switched capacitor 310 increases because VBATT_LO goes lower. Eventually, the amplified differential voltage drop ΔV across switched capacitor 310 will exceed $V_{thresh}$ 318, causing comparator output 313 to output a logical high. In an embodiment, $V_{thresh}$ 318 is approximately 500 mV.

As shown in FIG. 3A, a flip-flop 322 has a flip-flop clock input 323 coupled to comparator output 313 so that flip-flop 322 changes state each time comparator output 313 goes high. Flip-flop output 315 controls first switch 302 and fourth switch 308. Flip-flop output 315 is also coupled to an inverter 330 to produce an inverted flip-flop output 325. Inverted flip-flop output 325 is coupled to a flip-flop "d" input 317. Inverted flip-flop output 325 also controls second switch 304 and third switch 306. Each time flip-flop 322 changes state, it triggers two switches to close and two switches to open, causing switched capacitor 310 to reverse polarity.

For example, if switched capacitor current integrator 210 has the configuration shown in FIG. 3B, and load 314 draws current from reservoir capacitor 312 so that the amplified differential voltage ΔV exceeds $V_{thresh}$ 318, comparator output 313 will go high, causing flip-flop 322 to change state. Upon changing state, flip-flop output 315 will trigger first and fourth switches 302 and 308 to open, and inverted flip-flop output 325 will trigger second and third switches 304 and 306 to close. Accordingly, switched capacitor 310 will reverse polarity so that it will now be configured in the second polarity between battery 110 and load 314, as shown in FIG. 3C. A fixed amount of charge is then transferred from battery 110 and switched capacitor 310 to reservoir capacitor 312 to replenish it.

The switches will remain in the FIG. 3C configuration until flip-flop 322 again changes state. Upon changing state, flip-flop output 315 will trigger first and fourth switches 302 and 308 to close, and inverted flip-flop output 325 will trigger second and third switches 304 and 306 to open. Accordingly, switched capacitor 310 will reverse polarity so that it will again be configured in the first polarity between battery 110 and load 314, as shown in FIG. 3B. A fixed amount of charge is again transferred from battery 110 and switched capacitor 310 to reservoir capacitor 312 to replenish it.

As shown in FIG. 3A, flip-flop output 315 is routed to a digital counter 324. Digital counter 324 accumulates the total number of switched capacitor cycles, which is the total number of times switched capacitor 310 reverses polarity. Because the total integrated current consumed by ICD 10 passes through switched capacitor 310, the total integrated current drawn from battery 110 is proportional to the switching frequency of switched capacitor 310. Each time flip-flop 322 changes state, causing switched capacitor 310 to reverse polarity, digital counter 324 increments the total number of switched capacitor cycles. The total integrated current, in Ampere-hours, drawn from battery 110, is proportional to the capacitance $C_{switch}$ of switched capacitor 310, threshold voltage $V_{thresh}$ 318, and the total number of switched capacitor cycles according to equation (1):

$$\text{Total integrated current} \propto C_{switch} \cdot V_{thresh} \cdot \text{Total number of switched capacitor cycles} \quad (1)$$

In FIG. 3A, digital counter 324 interfaces with microcontroller 60, shown in detail in FIG. 2, via a counter output 319. Microcontroller 60 reads the total number of switched capacitor cycles accumulated by digital counter 324 and determines the level of battery 110 depletion based on the total integrated current drawn by ICD 10, according to equation (1). In an embodiment, a clinician uses external device 102, shown in FIG. 2, to interface with microcontroller 60 through telemetry circuit 100 to retrieve battery 110 depletion data.

In an embodiment, switched capacitor current integrator 210 includes a bypass circuit (not shown) to bypass switched capacitor 310. The bypass circuit bypasses switched capacitor 310 (and its associated switching transistors 302, 304, 306 and 308) when high currents (e.g., currents in the range of tens of milliamperes to several amperes) are drawn from battery 110. An example bypass circuit includes a high-current FET that can be turned on when high current bypass is required. Examples of when high current bypass is required include shocking treatment, such as defibrillation, reformation of the shocking capacitors, and exercise of battery 110. The amount of current drawn during these operations is known and microcontroller 60 can adjust the count of the number of switched capacitor cycles accordingly. However, such adjustment is not required, because such high current operations typically constitute only a small portion (e.g., typically about one to five percent) of the total battery 110 usage. Lower background current operations constitute the majority of the current draw on battery 110.

Example Implementation of a Switched Capacitor Current Integrator

Figure 4A:
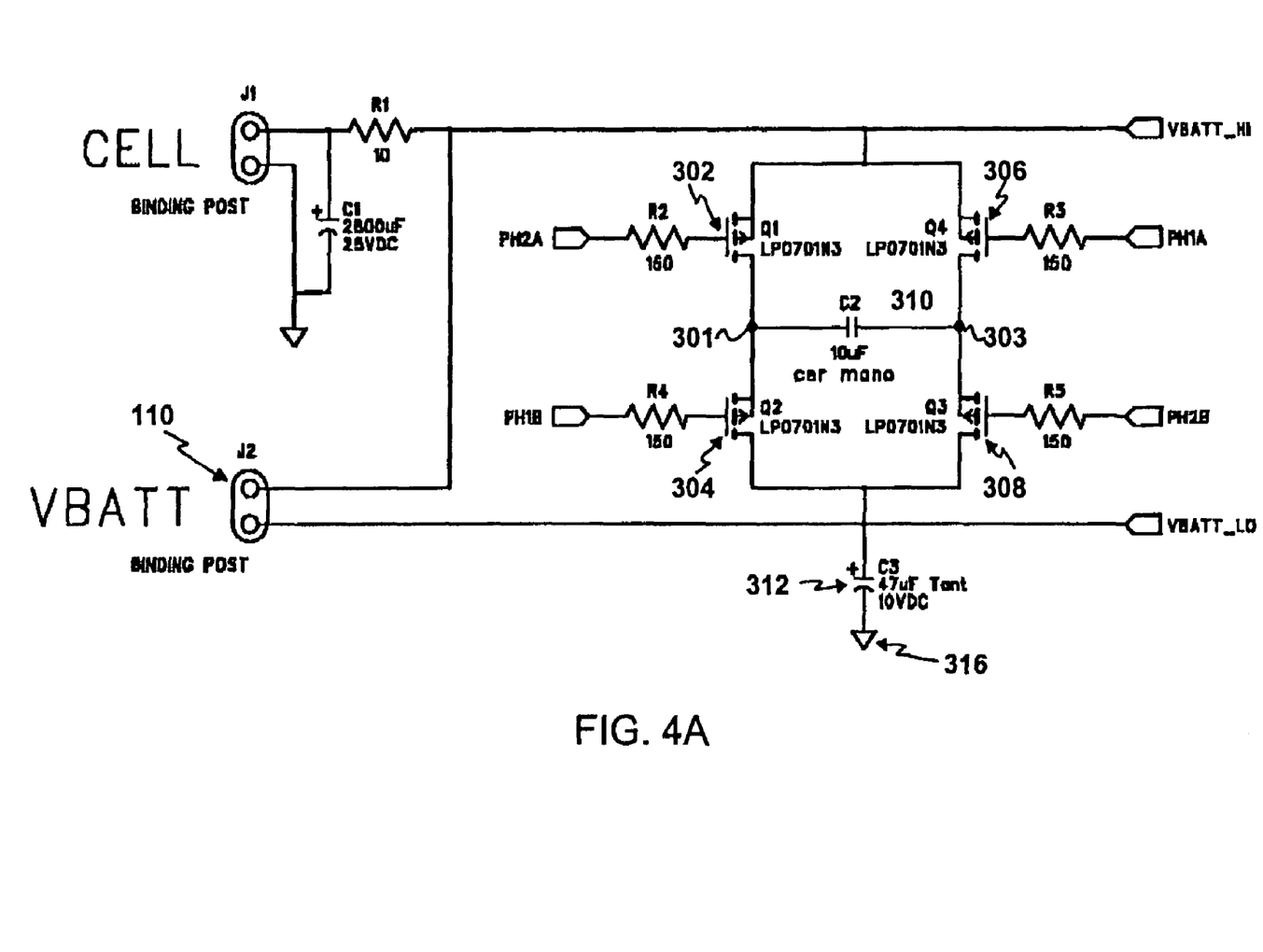
FIGS. 4A–4B show a circuit diagram of an example implementation of the switched capacitor current integrator shown in FIG. 3A, according to an example embodiment of the present invention.
Figure 4B:
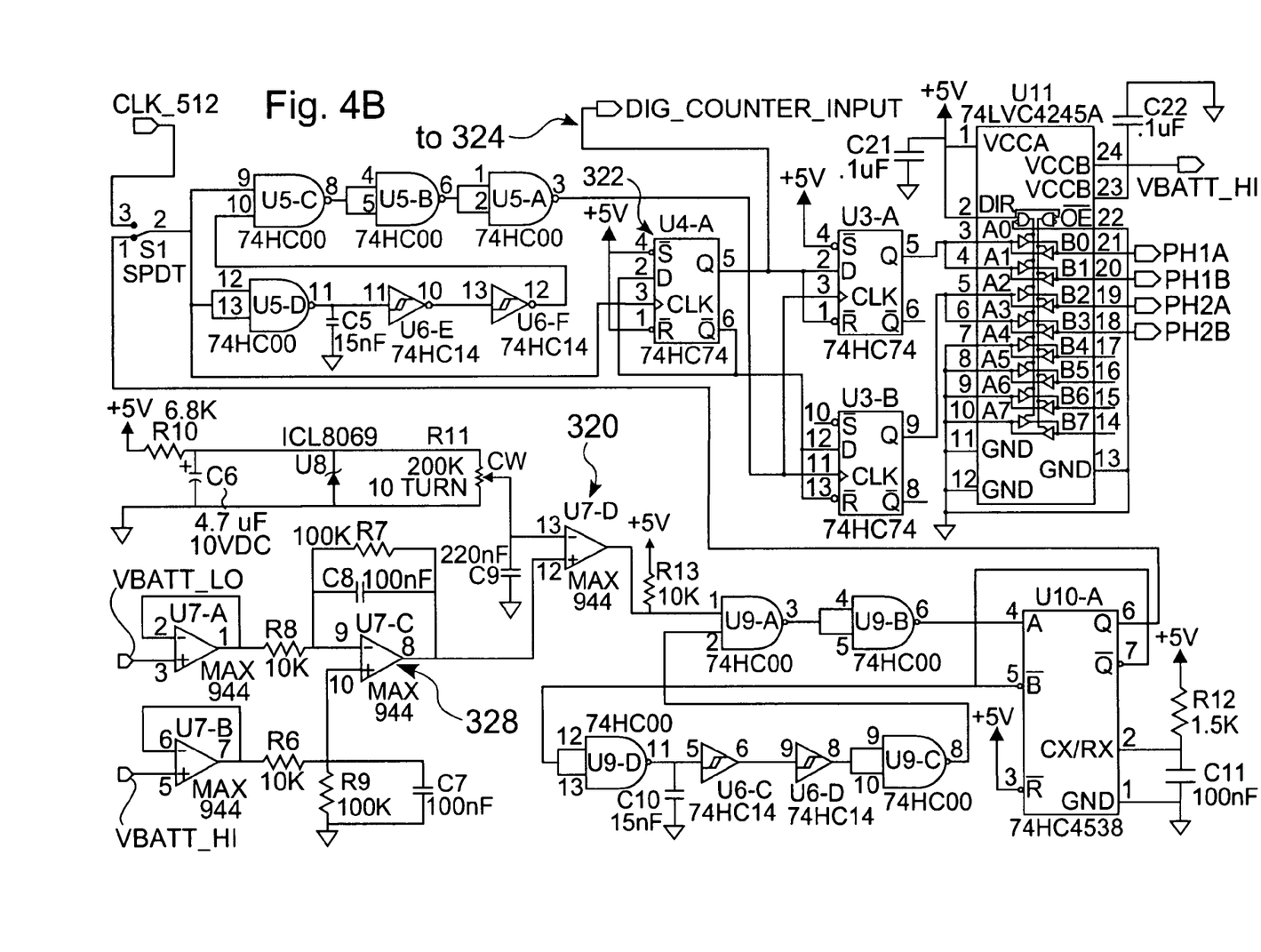
Figure 5:
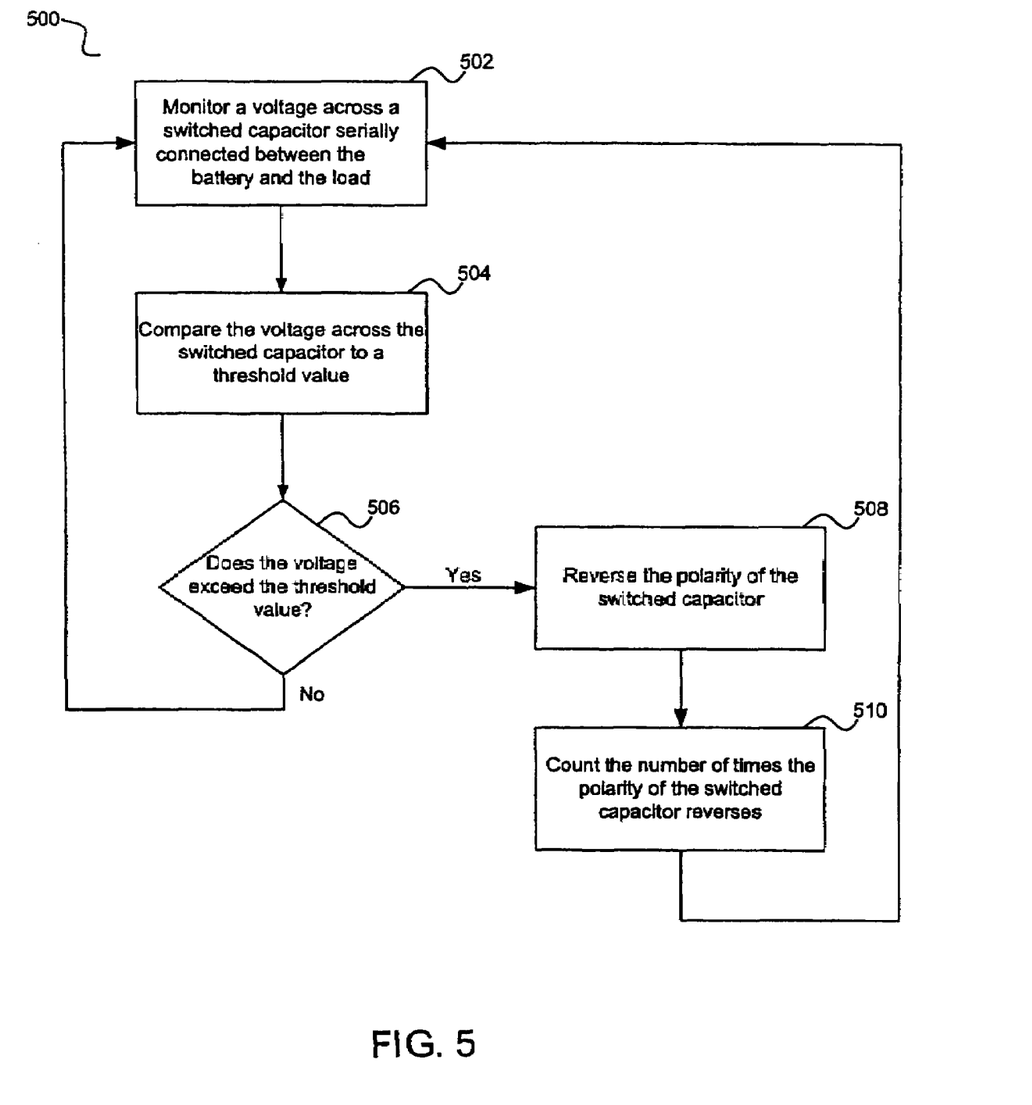
FIG. 5 is a flowchart illustrating a method for measuring battery depletion in an implantable medical device, according to example embodiments of the present invention.

FIGS. 4A–4B illustrate a circuit schematic for an example implementation of switched capacitor current integrator 210, shown in FIG. 3A, in accordance with an example embodiment of the present invention. The embodiment shown in FIGS. 4A–4B operates in the same manner as described above. Selected components of the switched capacitor current integrator of FIGS. 4A–4B are described below in reference to their corresponding elements shown in FIG. 3A.

FIG. 4A shows four switches Q1–Q4 arranged in an H-bridge configuration with a switched capacitor C2, which corresponds to switched capacitor 310 in FIG. 3A. Switches Q1–Q4 of FIG. 4A are implemented with metal oxide semiconductor field-effect transistors (MOSFETs). Switches Q1 and Q2, which correspond to first and second switches 302 and 304 in FIG. 3A, are coupled together at first node 301 and in series between battery 110 and a reservoir capacitor C3. Reservoir capacitor C3 corresponds to reservoir capacitor 312 in FIG. 3A. Switches Q4 and Q3, which correspond to third and fourth switches 306 and 308 in FIG. 3A, are coupled together at second node 303 and in series between battery 110 and reservoir capacitor C3. Switches Q1 and Q2 are arranged in a parallel configuration with switches Q4 and Q3. Switched capacitor C2 is coupled between first node 301 and second node 303 so that it is in the first polarity when only switches Q1 and Q3 are closed and in the second polarity when only switches Q2 and Q4 are closed.

In FIG. 4B, first and second buffers U7-A and U7-B, buffer inputs VBATT_LO and VBATT_HI, respectively, with a gain of approximately one. An amplifier U7-C, which corresponds to amplifier 328 of differential amplifier circuit 326 in FIG. 3A, is configured to have a gain of ten (i.e., R7/R8=10) and has an inverting input coupled to receive VBATT_LO and a non-inverting input coupled to receive VBATT_HI. A comparator U7-D has a non-inverting input coupled to receive the amplified differential voltage (VBATT_HI minus VBATT_LO) generated by amplifier U7-C. Comparator U7-D has an inverting input coupled to a threshold voltage. Comparator U7-D corresponds to comparator 320 in FIG. 3A, and compares the amplified differential voltage (VBATT_HI minus VBATT_LO) to the threshold voltage. In this example embodiment, the threshold is set to about 500 mV. Thus, given the 10× gain of the amplifier circuit, a voltage of 50 mV across the switched capacitor will cause the comparator to trip.

A flip-flop U4-A is shown in FIG. 4B, which corresponds to flip-flop 322 in FIG. 3A. Flip-flop U4-A is configured to change state when the amplified differential voltage (VBATT_HI minus VBATT-LO) exceeds the threshold voltage. Built into flip-flop U4-A is inverter 330, shown in FIG. 3A. Each time flip-flop U4-A changes state, it triggers two switches of array of four switches Q1–Q4 to open and two switches to close, and causes switched capacitor C2 to reverse polarity. In FIG. 4B, flip-flop U4-A has an output DIG_COUNTER_INPUT that is coupled to a digital counter 324 (not shown in FIG. 4B but shown in FIG. 3A). As described above, digital counter 324 accumulates the number of times switched capacitor C2 reverses polarity. The number of times is proportional to the total integrated current drawn from battery 110 and indicative of the level of battery 110 depletion.

Method for Measuring Total Integrated Current Drawn from a Battery

FIG. 5 illustrates a method 500 for measuring the total integrated current drawn from a battery in order to, for example, determine the level of battery depletion. In step 502, a differential voltage drop across a switched capacitor, serially connected between a battery and a load, is monitored. The differential voltage drop across the switched capacitor is compared to a threshold value in steps 504 and 506. In an embodiment, step 504 further includes the step of amplifying the differential voltage. If the differential voltage does not exceed the threshold value in step 506, then monitoring resumes in step 502.

When the load draws current, a reservoir capacitor becomes depleted and the differential voltage increases until eventually the differential voltage exceeds the threshold value. When the differential voltage exceeds the threshold value, the polarity of the switched capacitor is reversed in step 508. In an embodiment, step 508 includes the steps of opening a closed first pair of switches and closing an open second pair of switches (connected in an H-bridge configuration) in order to reverse the polarity of the switched capacitor, as described above. In step 510, the number of times the switched capacitor reverses polarity is counted. After step 510, monitoring resumes in step 502 and the cycle repeats as further power consumption by the load depletes the reservoir capacitor and again triggers the switched capacitor to reverse polarity.

The total integrated current consumed by the load passes through the switched capacitor. Accordingly, the total integrated current consumed by the load is proportional to the switching frequency of the switched capacitor, which is measured in step 510 by counting the total number of times the switched capacitor reverses polarity. In an embodiment, method 500 further includes the step of determining the depletion state of the battery based on the number of times the capacitor reverses polarity.

In the example embodiment depicted in FIGS. 4A–4B, with a typical load current in the range of 10 μA to 10 mA, a switched capacitor having a capacitance of 10 μF, and a threshold voltage of 50 mV as measured at the switched capacitor, the current integrator will have a switching frequency in the range of about 5 Hz to 5 kHz. Given a typical battery capacity of about 1.0 A-hour, a suitable digital counter would have 31 bits (to accommodate the $1.8 \times 10^9$ counts required to reach 1.0 A-hour). In such an example, if battery replacement is desired after 0.9 A-hours have been expended, then a count of $1.62 \times 10^9$ counts could be preselected to indicate a suitable battery replacement threshold.

CONCLUSION

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed is:

1. An apparatus for measuring battery depletion in an implantable medical device comprising:
   a capacitor disposed in series connection between the battery and a load;
   means for switching polarity of said capacitor; and
   means for generating an indication of depletion of the battery based on a number of times said capacitor switches polarity.

2. The apparatus of claim 1, wherein said switching means comprises four switches arranged in an H-bridge configuration.

3. The apparatus of claim 1, wherein said switching means comprises:
   a first transistor pair having first and second transistors connected at a first node, said first transistor pair being disposed in series between the battery and said load; and a second transistor pair having third and fourth transistors connected at a second node, said second transistor pair being disposed in series between the battery and said load, wherein said first and second transistor pairs are connected in a parallel arrangement with respect to one another, and wherein said capacitor is connected between said first and second nodes such that said capacitor is connected in a first polarity between the battery and said load when only said first and fourth transistors conduct, and said capacitor is connected in a second polarity between the battery and said load when only said second and third transistors conduct.

4. The apparatus of claim 3, wherein said generating means comprises:

a digital counter that counts said number of times said capacitor switches polarity.

5. The apparatus of claim 1, further comprising:

a bypass circuit coupled across said capacitor.

6. The apparatus of claim 1, further comprising:

means for monitoring a voltage across said capacitor and for causing said switching means to switch based on a comparison of said voltage to a threshold value.

7. The apparatus of claim 6, wherein said monitoring means comprises:

an amplifier circuit to amplify said voltage to produce an amplified voltage;

a comparator to compare said amplified voltage to said threshold value; and a flip-flop responsive to said comparator, said flip-flop changing state each time said amplified voltage exceeds said threshold value.

8. The apparatus of claim 7, wherein said switching means switches polarity of said capacitor each time said flip-flop changes state.

9. The apparatus of claim 8, wherein said switching means comprises four switches arranged in an H-bridge configuration.

10. The apparatus of claim 9, wherein said switching means comprises:

a first transistor pair having first and second transistors connected at a first node, said first transistor pair being disposed in series between the battery and said load; and a second transistor pair having third and fourth transistors connected at a second node, said second transistor pair being disposed in series between the battery and said load, wherein said first and second transistor pairs are connected in a parallel arrangement with respect to one another, and wherein said capacitor is connected between said first and second nodes such that said capacitor is connected in a first polarity between the battery and said load when only said first and fourth transistors conduct, and said capacitor is connected in a second polarity between the battery and said load when only said second and third transistors conduct.

11. The apparatus of claim 10, wherein said generating means comprises:

a digital counter that counts the number of times said flip-flop changes state.

12. An apparatus for measuring current supplied by a battery to a load, comprising:

a first switch pair having first and second switches connected to one another at a first node, said first switch pair being disposed in series between the battery and the load;

a second switch pair having third and fourth switches connected to one another at a second node, said second switch pair being disposed in series between the battery and the load, wherein said first and second switch pairs are connected in a parallel arrangement with respect to one another;

a capacitor connected between said first and second nodes such that said capacitor is connected in a first polarity between the battery and the load when only said first and fourth switches are closed, and said capacitor is connected in a second polarity between the battery and the load when only said second and third switches are closed;

a comparator circuit to cause said switches to reverse polarity of said capacitor based on a comparison of a voltage across said capacitor to a threshold value; and a counter to count a number of times that said capacitor reverses polarity, said count being indicative of current drawn from the battery.

13. The apparatus of claim 12, wherein said switches are transistors.

14. The apparatus of claim 13, wherein said transistors are MOSFETs.

15. The apparatus of claim 12, wherein said comparator circuit comprises:

an amplifier to amplify said voltage to produce an amplified voltage;

a comparator to compare said amplified voltage to said threshold value; and a flip-flop responsive to said comparator, said flip-flop changing state each time said amplified voltage exceeds said threshold value.

16. A method for measuring battery depletion in an implantable medical device, comprising:

monitoring a voltage across a capacitor serially connected between the battery and a load;

comparing said voltage to a threshold value;

switching polarity of said capacitor when said voltage exceeds said threshold value; and counting a number of times said capacitor switches polarity, wherein said number of times is proportional to an amount of charge transferred from said battery over time.

17. The method of claim 16, wherein said step of switching polarity comprises:

opening a closed first pair of switches; and closing an open second pair of switches.

18. The method of claim 16, wherein said capacitor is connected between a first switch pair and a second switch pair in an H-bridge configuration such that closing only a first switch of said first switch pair and only a fourth switch of said second switch pair causes current to flow through said capacitor in a first direction, and closing only a second switch of said first switch pair and only a third switch of said second switch pair causes current to flow through said capacitor in a second direction, and wherein said step of switching polarity comprises:

opening a closed one of said first and second switches;

opening a closed one of said third and fourth switches;

closing an open one of said first and second switches; and
closing an open one of said third and fourth switches.

19. The method of claim 18, further comprising:
determining a depletion state of said battery based on said number of times said capacitor switches polarity.

20. The method of claim 16, further comprising:
determining a depletion state of said battery based on said number of times said capacitor switches polarity.

* * * * *